United States Patent [19]

Bailey

[11] Patent Number: 5,048,524

[45] Date of Patent: Sep. 17, 1991

[54] BLOOD PARAMETER MEASUREMENT

[75] Inventor: Wilber H. Bailey, Leucadia, Calif.

[73] Assignee: Camino Laboratories, Inc., San Diego, Calif.

[21] Appl. No.: 318,779

[22] Filed: Mar. 3, 1989

[51] Int. Cl.$^5$ .............................................. A61B 5/14
[52] U.S. Cl. .................................................. 128/634
[58] Field of Search ........................ 128/633, 634, 665

[56] References Cited

U.S. PATENT DOCUMENTS

| 3,068,742 | 12/1962 | Hicks et al. | 128/634 |
| 3,123,066 | 3/1964 | Brumley | 128/634 |
| 3,638,640 | 2/1972 | Shaw | 128/2 R |
| 3,799,672 | 3/1974 | Vurek | 356/41 |
| 3,802,776 | 4/1974 | Tchang | 356/41 |
| 3,807,390 | 4/1974 | Ostrawski et al. | 128/634 |
| 3,814,081 | 6/1974 | Mori | 128/634 |
| 4,050,450 | 9/1977 | Polanni et al. | 128/634 |
| 4,066,361 | 1/1978 | Achter | 356/41 |
| 4,086,915 | 5/1978 | Kofsky et al. | 128/2 L |
| 4,114,604 | 9/1978 | Shaw et al. | 128/2 L |
| 4,167,331 | 9/1979 | Nielson | 356/39 |
| 4,266,554 | 5/1981 | Hamaguri | 128/633 |
| 4,273,442 | 6/1981 | Lübbers | 356/326 |
| 4,303,336 | 12/1981 | Cullis | 356/39 |
| 4,304,488 | 12/1981 | Asakura et al. | 356/39 |
| 4,403,038 | 9/1983 | Asakura et al. | 436/16 |
| 4,407,290 | 10/1983 | Wilber | 128/633 |
| 4,416,285 | 11/1983 | Shaw et al. | 128/634 |
| 4,449,535 | 5/1984 | Renault | 128/634 |
| 4,523,279 | 6/1985 | Sperinde et al. | 364/416 |
| 4,621,643 | 11/1986 | New, Jr. et al. | 128/633 |
| 4,622,974 | 11/1986 | Coleman et al. | 128/634 |
| 4,623,248 | 11/1986 | Sperinde | 356/41 |
| 4,651,741 | 3/1987 | Passafaro | 128/633 |
| 4,776,340 | 10/1988 | Moran et al. | 128/634 |
| 4,803,992 | 2/1989 | Lemelson | 128/634 |

FOREIGN PATENT DOCUMENTS 0004155 6/1988 World Int. Prop. O. .......... 128/633

OTHER PUBLICATIONS

Merrick et al., Hewlett-Packard Journal, vol. 28, No. 2, Oct. 1976, pp. 2-9.
"An Integrated Circuit-Based Optical Sensor for In Vivo Measurement of Blood Oxygenation", by J. M. Schmitt, J. D. Miendl, F. G. Mihm, IEEE Transactions on Biomedical Engineering, vol. BME-33, No. 2, Feb. 1986, pp. 98-107.

Primary Examiner—Kyle L. Howell
Assistant Examiner—John Hanley
Attorney, Agent, or Firm—Fulwider, Patton, Lee & Utecht

[57] ABSTRACT

A method and apparatus for measuring the oxygen saturation level and hematocrit of human blood in real time. A catheter having a notch in its tip is inserted into a blood vessel and guided to a desired location in the body of a patient. Bursts of light at each of three wavelengths are transmitted through the blood in the notch. The intensities of the bursts of light after transmission are utilized along with a set of molecular exinction coefficients and optical scattering coefficients to calculate the oxygen level and hematocrit. The light is provided by a set of LEDs in a housing connected to the catheter and the intensity of the transmitted light is measured by a photocell in the same housing. Optical fibers transmit the light through the catheter between the housing and the notch. Characterization resistors in the housing are encoded with characteristics such as the wavelengths of the LEDs and the width of the notch. In an alternate embodiment blood circulating through a loop out of the patient's body is passed through a chamber and is exposed to the light.

40 Claims, 5 Drawing Sheets

BLOOD PARAMETER MEASUREMENT

BACKGROUND OF THE INVENTION

The present invention relates generally to the measurement of parameters of human blood and more particularly to an apparatus and method for measuring blood parameters such as oxygen saturation level and hematocrit in a living patient.

A continuous and adequate supply of oxygen is essential to health. Diminution or interruption of the oxygen supply, even for a brief moment, can result in unconsciousness, injury to vital organs, and death. Thus it is often medically necessary to monitor the amount of oxygen being received by the body, especially during critical surgical procedures in which there is an inherent risk of interruption of the oxygen supply.

Monitoring the oxygen being received by the body is accomplished by measuring the oxygen content of the blood, because it is the blood that carries oxygen from the lungs to all parts of the body. Oxygen in the blood is actually carried by hemoglobin, a protein in red blood cells. The blood comes into contact with free oxygen in the lungs, and the hemoglobin combines with molecules of the free oxygen. As the blood flows it carries the hemoglobin and the oxygen throughout the body. The oxygen is released by the hemoglobin to the muscles and other bodily organs where it is used.

Hemoglobin which is combined with oxygen is called oxyhemoglobin; hemoglobin which is not combined with oxygen is known as deoxyhemoglobin or reduced hemoglobin. At any given time and location in the body, a certain fraction $s$ of the hemoglobin in the blood is oxyhemoglobin and the remaining fraction $1-s$ is reduced hemoglobin. The oxygen content of a sample of blood is usually expressed as a saturation level percentage, which is the ratio of oxyhemoglobin to total hemoglobin. If the fraction $s$ of oxyhemoglobin in a certain sample of blood is 25%, that sample is said to be 25% saturated with oxygen or to have a blood oxygen level of 25%.

The total amount of oxygen in the blood is determined not only by the oxygen saturation level but also by the total amount of hemoglobin present in the red blood cells. Thus, it is important to know the hemoglobin concentration (hematocrit) $h$, as well as the saturation level in order to determine how much oxygen is being carried by the blood.

It is a relatively straight-forward procedure to measure the oxygen saturation level $s$ and hematocrit $h$ of a sample of blood which has been removed from a patient, for example by means of a hypodermic needle, and transported in a test tube or the like to a medical laboratory. Known methods of laboratory analysis provide highly accurate results, and for many medical purposes these methods are entirely sufficient. However, the process of removing blood from a patient and analyzing it in a laboratory takes time, and if it is necessary to monitor the amount of oxygen in the blood on a real-time basis, as is often the case during surgery, such a procedure is not adequate.

In addition, it is sometimes necessary to monitor the amount of oxygen being received by a specific organ such as the heart. This need may arise, for example, during certain kinds of coronary surgery. Analysis of a sample of blood which has been taken from a bodily location such as an artery of an arm or a leg does not provide the required information respecting the amount of oxygen being provided to the heart or some other internal organ.

Both oxyhemoglobin and reduced hemoglobin absorb light, but certain wavelengths are absorbed more readily by the one than by the other. This difference is easily seen with the unaided eye in that freshly oxygenated blood (in which most of the hemoglobin is oxyhemoglobin) is bright red in color whereas blood from which the oxygen has been removed (most of the hemoglobin being reduced hemoglobin) is darker and has a bluish hue. Accordingly, various devices and methods have been proposed for determining the amount of oxygen in the blood by measuring the attenuation of a beam of light as it passes through a sample of blood.

U.S. Pat. No. 3,638,640, issued to Robert F. Shaw on Feb. 1, 1972, typifies a class of such proposals in which light is directed through an ear lobe or the like. Shaw seeks to determine the oxygen level of the blood in the ear lobe by measuring the attenuation of the light at each of a plurality of wavelengths as the light passes through the ear lobe.

A somewhat similar device is disclosed in U.S. Pat. No. 4,621,643, issued to William New, Jr., et al. on Nov. 11, 1986. This device utilizes the principles of the Shaw invention but with the addition of an encoding resistor which indicates the wavelengths of the light sources in the device to facilitate the calculation of the oxygen level of the blood.

U.S. Pat. No. 3,799,672, issued to Gerald G. Vurek on Mar. 26, 1974 illustrates another device which is based on the principle of attenuation of light passing through a sample of blood. Instead of directing the light through an ear lobe or other bodily appendage, Vurek passes the light through a sample of blood circulating from a patient through a plastic tube outside the body.

In another class of such devices, two optical fibers are introduced into a blood vessel. Light passes into the bloodstream through one of the fibers; some of this light is reflected back through the other fiber, and the oxygen level of the blood is determined by measuring the intensity of the reflected light at each of a plurality of wavelengths. U.S. Pat. No. 4,623,248 issued to John M. Sperinde on Nov. 18, 1986 is illustrative of such devices.

It will be apparent from the foregoing that there remains a need for an accurate way to measure not only the oxygen saturation level but also the hematocrit of human blood on a real-time basis and at a desired location in the body of a patient.

SUMMARY OF THE INVENTION

The present invention provides an apparatus and method for measuring blood parameters such as oxygen saturation level and hematocrit in real time at any desired location in the body of a living patient by directing light through a blood sample of known width and calculating the parameters based on a set of molecular extinction coefficients and optical scattering coefficients.

Briefly and in general terms, apparatus according to the invention includes a receptacle into which blood flows, a light source such as a set of light-emitting diodes ("LEDs") which provide light at known wavelengths, a guide for guiding the light into the receptacle, a receiver for receiving the light after it has passed through the receptacle, a sensor for measuring the intensity of the light after it has passed through the receptacle, and a computer which computes a parameter of the blood according to the measured intensity of the light. The sensor may also provide a reference measurement of the intensity of the incident light as provided by the LEDs.

The invention is preferably embodied in a catheter having a distal tip which can be guided through the blood vessels to a desired location in the body. A notch located near the tip of the catheter serves as the receptacle. An optical fiber guides the light from the LEDs to the notch and another fiber guides the light from the notch back to the sensor. An optional lumen extends through the catheter to the notch whereby a flushing fluid can be injected through the tubelet to flush the notch.

The catheter preferably includes a built-in characterization device for providing a characteristic value, such as the width of the notch or the wavelengths of the light provided by the LEDs, for use by the computer.

In an alternate embodiment of the invention, blood circulates out of the body of the patient, through a measurement chamber, and back to the patient. The light passes through the measurement chamber and the blood therein. A constrictor in the circulation tubing creates a pressure drop so that the blood can be withdrawn from an artery at a relatively high pressure and returned to a vein at a relatively low pressure.

The invention provides a method of measuring blood parameters by means of the apparatus described above. The method comprises the steps of passing sequential bursts of light through the blood, each burst characterized by one of a plurality of preselected wavelengths; measuring the intensity of each burst of light after it has passed through the blood; and computing a parameter of the blood according to these measured intensities. Preferably, the sequential bursts of light are also passed through a calibration fluid to provide a set of measured calibration intensities for use in performing the computations.

A high degree of accuracy is achieved in part by using optical scattering coefficients which are characteristic of whole blood in addition to molecular extinction coefficients of oxyhemoglobin and reduced hemoglobin in performing the calculations.

Other aspects and advantages of the present invention will become apparent from the following detailed description, taken in conjunction with the accompanying drawings, illustrating by way of example the principles of the invention.

DESCRIPTION OF THE PREFERRED EMBODIMENTS

A. Introduction

As shown in the drawings for purposes of illustration, the invention is embodied in a novel method and apparatus for measuring a blood parameter such as oxygen concentration level and hematocrit.

Various devices have been proposed for measuring blood oxygen level by transmitting two or more successive bursts of light, each at a different wavelength, through a sample of blood and calculating the oxygen level according to the attenuation of the light. However, these devices have not satisfied the need for an accurate way to measure blood parameters on a real-time basis and at a desired location in the body of a patient.

In accordance with the invention, a catheter having a receptacle or notch near its distal tip is adapted for insertion into a blood vessel. The tip is guidable to a desired location in the body of the patient. Light from a plurality of LEDs is guided through the notch and any blood therein. The attenuation of the light by the blood is measured, and the desired blood parameter is calculated according to a plurality of predetermined molecular extinction coefficients and optical scattering coefficients.

Apparatus embodying the invention provides a simple and accurate way to measure blood oxygen level and hematocrit in real time at any desired location in the body or (by means of an alternate embodiment of the invention) in blood circulating outside the body. The measurements are not affected by any reflections from blood vessel walls or the like. The use of reference measurements and optical scattering coefficients in performing the calculations leads to a high degree of accuracy. The apparatus is economical to manufacture due in part to inclusion of an optional characterization device and hence is disposable after a single use.

In the following paragraphs, the Bouguer-Lambert law, which provides the mathematical basis for computing the blood oxygen level s and hematocrit h of a sample of blood by means of the attenuation of light passing through the blood, will be discussed and an equation which can be solved for s and h will be derived. Next, a method for determining the molecular extinction coefficients and optical scattering coefficients of human blood will be set forth. Finally, preferred embodiments of the apparatus and method of the invention will be described, including a procedure for solving the above-mentioned equation for s and h.

B. The Bouguer-Lambert Law

According to the Bouguer-Lambert Law of analytical chemistry (this law is sometimes referred to as "Lambert's Law" or as "Beer's Law"), the intensity of a beam of monochromatic light transmitted through a light-absorbent substance is exponentially related to the width of the substance through which the light is transmitted and to a "molecular extinction coefficient" which is a function of the wavelength of the light and the nature of the substance. In mathematical terms:

$$I = I_0 e^{-\beta d} \tag{1}$$

where:

I = the measured intensity of the light through the substance;
$I_0$ = the intensity of the incident light;
e = 2.718 ... (the natural logarithm base);
$\beta$ = the molecular extinction coefficient of the substance at the wavelength of the incident light; and
d = the width of the substance through which the light passes.

For a substance consisting of a mixture of a light-absorbent liquid and a transparent liquid, equation (1) becomes $$I = I_0 e^{-\beta cd} \tag{2}$$

where:

c = the concentration of the absorbent liquid in the mixture.

For a substance consisting of a mixture of two light-absorbent liquids, equation (1) becomes $$I = I_0 e^{-\beta_1 c_1 d} e^{-\beta_2 c_2 d} \tag{3}$$

where:

$\beta_1$ = the molecular extinction coefficient of the first liquid;
$c_1$ = the concentration of the first liquid;
$\beta_2$ = the molecular extinction coefficient of the second liquid; and
$c_2$ = the concentration of the second liquid.

If there are no other substances present in the mixture, then $c_1 + c_2 = 1$, or $c_2 = 1 - c_1$, and Equation (3) can be expressed as follows:

$$I = I_0 e^{-\beta_1 c_1 d} e^{-\beta_2 (1-c_1) d} \tag{3a}$$

As discussed above, human blood comprises a mixture of oxyhemoglobin, reduced hemoglobin and other components. Both oxyhemoglobin and reduced hemoglobin absorb light, but each has a different molecular extinction coefficient.

The other components of the blood are generally transparent; however, these components have a scattering effect on light, and the magnitude of this effect is a function of the wavelength of the incident light and the oxygen saturation s of the blood. This scattering effect does not follow the Bouguer-Lambert law but can be expressed as an exponential function of an "optical scattering coefficient" which is a function of the oxygen saturation level s of the blood.

In view of the above considerations, for human blood equation (1) takes the form:

$$I = I_0 e^{-\beta_s shd} e^{-\beta_r (1-s) hd} e^{-\beta_{z(s)}} \tag{4}$$

where:

| | |
|---|---|
| $\beta_s$ | = molecular extinction coefficient of oxyhemoglobin; |
| $\beta_r$ | = molecular extinction coefficient of reduced hemoglobin; |
| $\beta_{z(s)}$ | = optical scattering coefficient as a function of s; |
| h | = concentration of hemoglobin in the blood (expressed in units of hematocrit); and |
| s | = ratio of oxyhemoglobin to total hemoglobin. |

Dividing both sides of equation (4) by $I_0$, taking the natural logarithm of both sides, and multiplying through by −1 yields the following equation:

$$\ln I_0 - \ln I = \beta_s shd + \beta_r (1-s) hd + \beta_{z(s)} \tag{5}$$

Measuring the values of the intensity I of each of three bursts of light passing through a sample of blood, one burst at each of three different wavelengths $\lambda_1$, $\lambda_2$ and $\lambda_3$ at which the values of $\beta_s$, $\beta_r$ and $\beta_{z(s)}$ are known, yields a set of three equations of the form of Equation (5):

$$\ln I_{01} - \ln I_1 = \beta_{s1} shd + \beta_{r1}(1-s)hd + \beta_{z1(s)} \tag{5a}$$

$$\ln I_{02} - \ln I_2 = \beta_{s2} shd + \beta_{r2}(1-s)hd + \beta_{z2(s)} \tag{5b}$$

$$\ln I_{03} - \ln I_3 = \beta_{s3} shd + \beta_{r3}(1-s)hd + \beta_{z3(s)} \tag{5c}$$

where:

| | |
|---|---|
| $I_{01}$ | = intensity of incident light at wavelength $\lambda_1$; |
| $I_{02}$ | = intensity of incident light at wavelength $\lambda_2$; |
| $I_{03}$ | = intensity of incident light at wavelength $\lambda_3$; |
| $I_1$ | = intensity of light at wavelength $\lambda_1$ after passing through blood; |
| $I_2$ | = intensity of light at wavelength $\lambda_2$ after passing through blood; |
| $I_3$ | = intensity of light at wavelength $\lambda_3$ after passing through blood; |
| $\beta_{s1}$ | = coefficient of oxyhemoglobin at wavelength $\lambda_1$; |
| $\beta_{s2}$ | = coefficient of oxyhemoglobin at wavelength $\lambda_2$; |
| $\beta_{s3}$ | = coefficient of oxyhemoglobin at wavelength $\lambda_3$; |
| $\beta_{r1}$ | = coefficient of reduced hemoglobin at wavelength $\lambda_1$; |
| $\beta_{r2}$ | = coefficient of reduced hemoglobin at wavelength $\lambda_2$; |
| $\beta_{r3}$ | = coefficient of reduced hemoglobin at wavelength $\lambda_3$; |
| $\beta_{z1(s)}$ | = optical scattering coefficient at wavelength $\lambda_1$ and blood oxygen level s; |
| $\beta_{z2(s)}$ | = optical scattering coefficient at wavelength $\lambda_2$ and blood oxygen level s; and |
| $\beta_{z3(s)}$ | = optical scattering coefficient at wavelength $\lambda_3$ and blood oxygen level s. |

Equations 5(a), 5(b) and 5(c) together constitute a set of equations which can be solved for s and h according to the method of the invention as described hereafter.

C. Determining the Molecular Coefficients of Extinction and Scattering Coefficients The molecular coefficients of extinction may be determined experimentally by measuring the attenuation of light of a known wavelength which is transmitted through a blood sample of known width d, hematocrit h and oxygen saturation level s.

A sample of whole blood is exposed to oxygen (for example by bubbling the oxygen through the sample) until the blood is 100% saturated (s = 1). Then the transmittance spectrum of the sample is measured (for example by means of a transmittance spectrometer). Next, the oxygen is removed from the blood (for example by bubbling nitrogen through the blood) until the blood is reduced to a very low oxygen concentration (s << 1). Then the transmittance spectrum is measured again. The transmittance spectrum for s = 0 is calculated from these measurements, for example by extrapolation by linear regression.

Next, the sample is hemolyzed, the transmittance spectra of the hemoglobin for s = 1 and s << 1 are measured, and the transmittance spectrum of the hemoglobin for s = 0 is calculated by extrapolation by linear regression. The transmittance spectra of the hemoglobin provide the molecular coefficients of extinction $\beta_s$ and $\beta_r$ of the hemoglobin for s = 1 and s = 0. ("Hemolyzing" the blood means breaking down the red blood cell structure and thereby causing the hemoglobin to go into solution in the plasma of the blood. This procedure has the effect of eliminating the optical scattering effect of the blood.)

More particularly, Equation (5) above provides the means for computing the molecular coefficients of extinction for hemolyzed blood for each wavelength of interest. Because there is no optical scattering effect in hemolyzed blood, $\beta_{z(s)}=0$ and therefore the last term of the right side of Equation (5) vanishes. For 100% oxygenated blood, s=1 and therefore the middle term of Equation (5) also vanishes and Equation (5) becomes:

$$\ln I_0 - \ln I = \beta_s shd \tag{5d}$$

where s=1; h, d, and $I_0$ have been measured; and I for a given wavelength is given by the transmittance spectrometer reading for that wavelength. Accordingly all the terms in Equation (5d) except $\beta_s$ are known and the equation can be solved for $\beta_s$ for that wavelength. This procedure is repeated for each wavelength of interest until a set of $\beta_s$, one for each wavelength of interest, have been computed.

Similarly, for hemolyzed blood from which all the oxygen has been removed, the first and third terms on the right side of Equation (5) vanish and Equation (5) becomes $$\ln I_0 - \ln I = \beta_r(1-s)hd \tag{5e}$$

where s=0; h, d, and $I_0$ have been measured; and I for a given wavelength is given by the transmittance spectrometer reading for that wavelength. All the terms in Equation (5e) except $\beta_r$ being known, the equation can be solved for $\beta_r$ for that wavelength. The procedure is repeated for each wavelength of interest until a set of $\beta_r$, one for each wavelength of interest, have been computed.

Once the above measurements and calculations have been performed, the optical scattering coefficients $\beta_{z(s)}$ for s=1 and s=0 at various wavelengths are readily calculated from the transmittance spectra of whole blood and of hemoglobin by algebraic techniques. For example, known values of $\beta_s$ and $\beta_r$ as determined above by solving Equations (5d) and (5e) for a given wavelength are substituted into Equation (5) and then Equation (5) is solved for $\beta_{z(s)}$ by using the values of I which were measured for whole blood at that wavelength to compute a set of $\beta_{z(s)}$ corresponding to s=1 and s=0 at various wavelengths.

More particularly, for 100% oxygenated whole blood, s=1 and therefore the middle term of Equation (5) vanishes and Equation (5) becomes:

$$\ln I_0 - \ln I = \beta_s shd + \beta_{z(s=1)} \tag{5f}$$

where s=1; h, d, and $I_0$ have been measured; $\beta_s$ has been determined in the manner set forth above; and I is given by the transmittance spectrometer reading. All the terms of Equation 5(f) except $\beta_{z(s=1)}$ being known, the equation can be solved for $\beta_{z(s=1)}$ for that wavelength. This procedure is repeated for each wavelength until a set of $\beta_{z(s=1)}$, one for each wavelength of interest, have been computed.

In an analogous fashion a set of $\beta_{z(s=0)}$ are determined for the various wavelengths of interest.

A transmittance spectrometer which can be used to carry out the above measurements comprises, for example, a light source which transmits light through a sample of blood having a precisely measured width, then through a diffraction grating onto a charge coupled device ("CCD") to obtain a signal which quantitatively indicates the absorption of light at various wavelengths. This signal is preferably digitized and provided to a computer which then computes the molecular extinction coefficients at any desired wavelength.

When all of the coefficients have been determined, they are stored in a table for use in determining the oxygen concentration level s and hematocrit h of a sample of blood according to the method of the invention as described hereafter.

D. The Apparatus of the Invention

Figure 1:
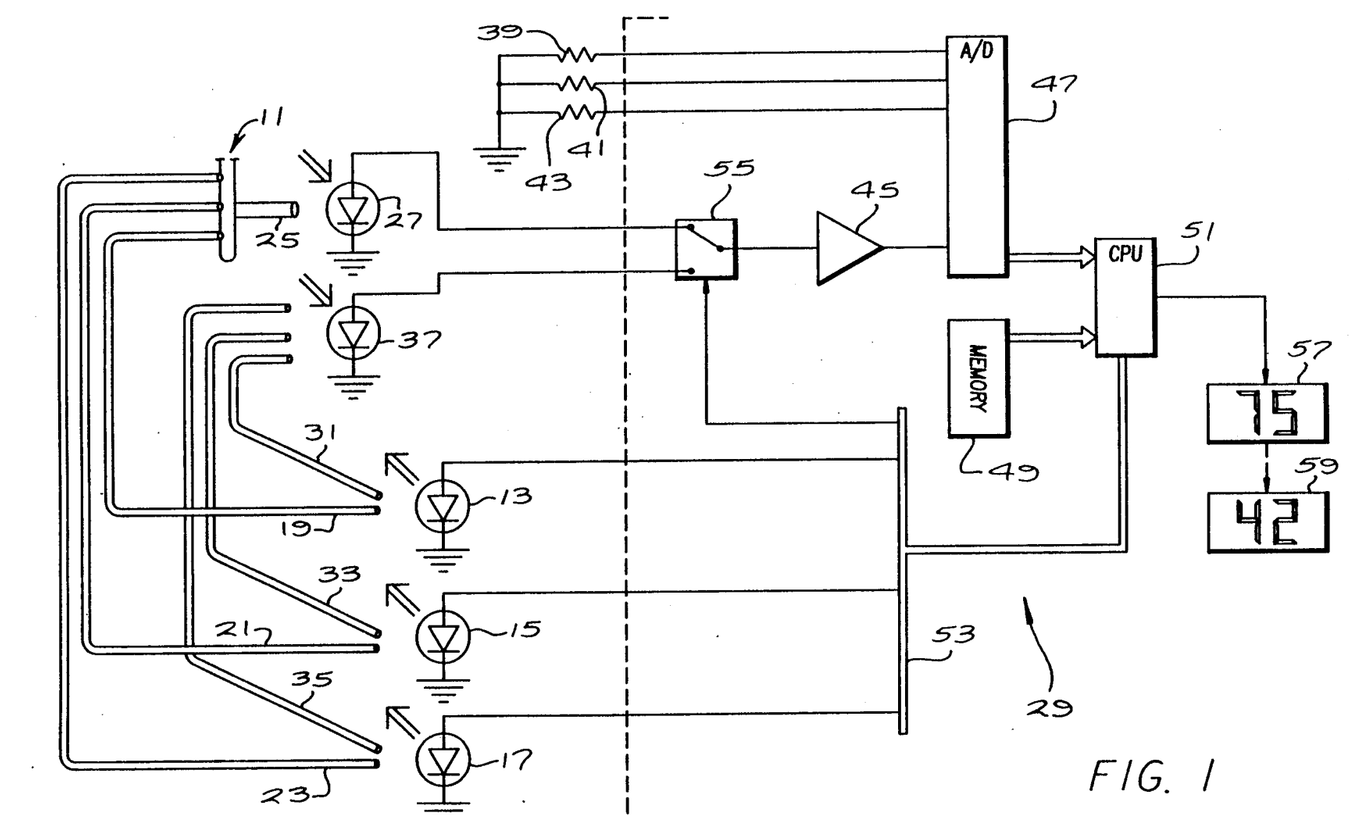
FIG. 1 is a diagrammatic illustration of apparatus for measuring a parameter of blood according to the invention.

As illustratively shown in FIG. 1, a preferred embodiment of apparatus for measuring a parameter of a sample of blood according to the invention comprises means defining a receptacle 11 for receiving a sample of blood; generating means such as a plurality of LEDs 13, 15 and 17 for generating bursts of optical energy, each burst characterized by one of a plurality of preselected wavelengths; guide means such as a plurality of optical fibers 19, 21 and 23 for guiding the energy into any blood in the receptacle 11; receiving means such as an optical fiber 25 for receiving the energy after it has passed through the blood in the receptacle 11; measuring means such as a measurement photocell 27 for measuring the intensity of each burst of received energy; and computing means generally designated 29, operative to compute the desired parameter of the blood according to the measured intensities of the received bursts of energy and a plurality of predetermined molecular extinction coefficients and optical scattering coefficients.

The apparatus preferably includes means such as a plurality of optical fibers 31, 33 and 35 and a reference photocell 37 to provide a reference indicative of the intensity of the optical energy as provided by the LEDs 13, 15 and 17. The reference is used to correct for any instability or drift of the intensity of the light source.

A characterization device such as a set of characterization resistors 39, 41 and 43 is preferably included for providing a characteristic value of the apparatus to the computing means 29. This characteristic value comprises, for example, the width d of the receptacle 11 and the values of the wavelengths $\lambda_1$, $\lambda_2$ and $\lambda_3$ of the light provided by the LEDs 13, 15 and 17.

The computing means 29 utilizes the reference and the characteristic value in performing the computations involved in finding s and h.

The computing means 29 preferably includes a logarithmic amplifier 45 which receives output signals from the photocells 27 and 37 and logarithmically amplifies these signals. Equations (5a), (5b) and (5c) above are based on the log of the measured light intensity, and therefore much pre-processing is accomplished by utilizing a logarithmic amplifier. In addition, such an amplifier is well adapted for a wide dynamic range of input signals; the amplifier preferably has a range of about ±4 decades. The log gain of the amplifier is nominally set to one volt per decade. Any errors due to such factors as temperature drift and component aging are measured and corrected by the microprocessor by means of techniques which are known to those skilled in the art.

An analog-to-digital ("A-to-D") converter 47 converts the amplified signals provided by the amplifier 45 into digital form. The A-to-D converter 47 also provides a digital signal indicative of the values of the characterization resistors 39, 41 and 43. A memory 49 stores digital representations of the molecular coefficients of extinction and the optical scattering coefficients of extinction.

A central processing unit ("CPU") 51 such as a microprocessor chip receives the digital signals from the A-to-D converter 47 and from the memory 49 and performs the computations. The CPU 51 controls the illumination of the LEDs 13, 15 and 17 through a control bus 53. The CPU 51 also controls which of the photocells 27 and 37 is connected to the amplifier 45 by a switching means 55. For purposes of illustration the switching means 55 is depicted as a mechanical switch, but a solid state switch or the like could be used instead.

The values of the blood oxygen level s and hematocrit h as computed by the CPU 51 are displayed on readouts 57 and 59. The values "75" and "42" shown in the figure are typical values which might be displayed as a result of the analysis of a typical sample of blood.

Figure 2:
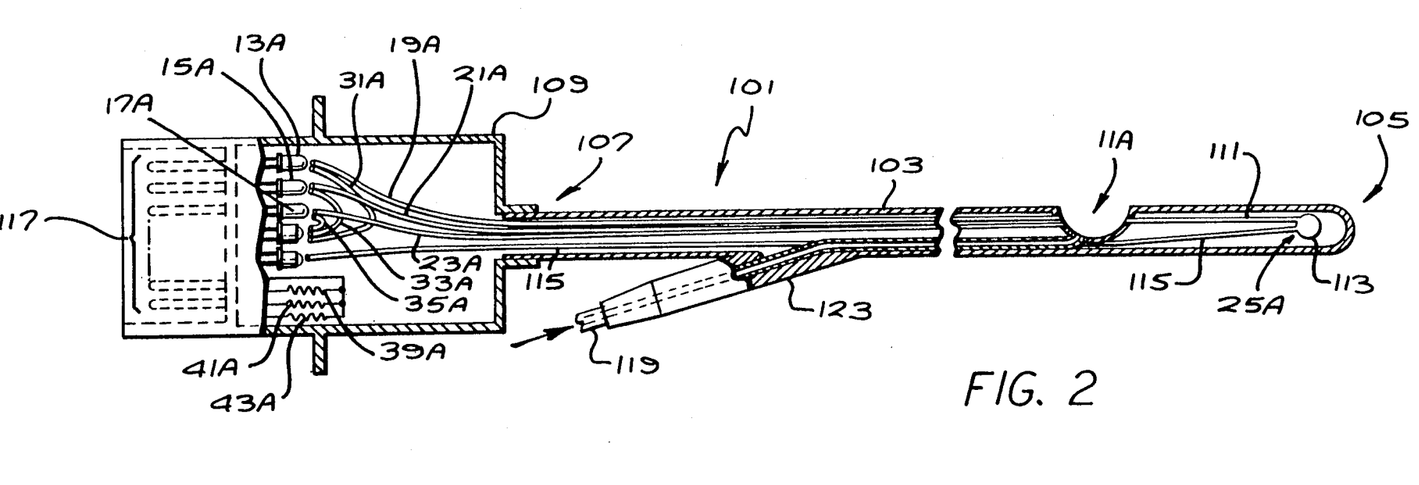
FIG. 2 is a pictorial diagram of a catheter embodying the apparatus of FIG. 1 as adapted for measuring a parameter of blood at a desired location in the body of a patient.
Figure 3:
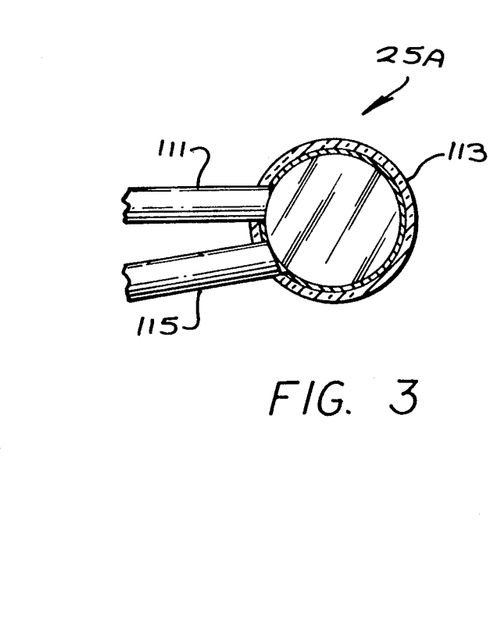
FIG. 3 is a closeup view of the mixing ball of the catheter of FIG. 2.
Figure 4:
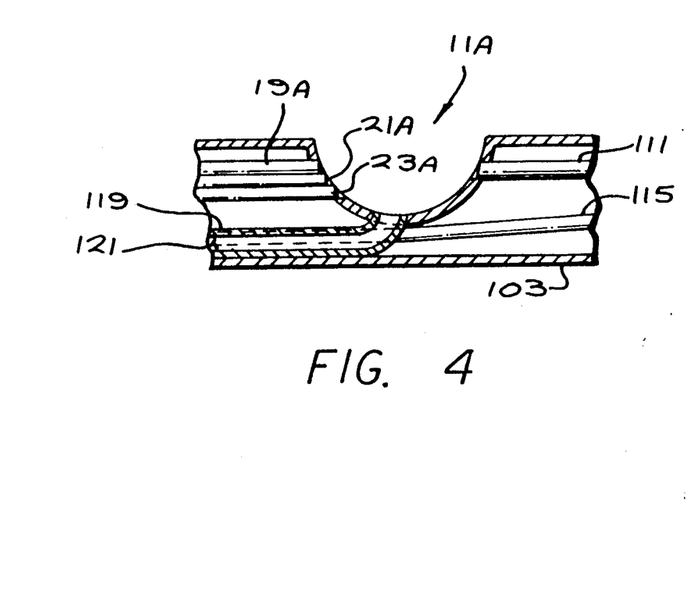
FIG. 4 is a closeup view of the receptacle of the catheter of FIG. 2.

The invention is preferably embodied in a catheter generally designated 101 as shown in FIGS. 2 through 4. Several of the components of this embodiment are analogous to components shown in the more general embodiment of FIG. 1, and for convenience such components are identified by the same reference numerals as their FIG. 1 counterparts plus the suffix "A".

The catheter 101 includes an elongated catheter tube 103 adapted for insertion into a body of a living being, a distal extremity 105 of the tube 103 being guidable to a desired location in the body and having a receptacle 11A shaped as a semicircular notch in the tube 103 for receiving a sample of blood at said location. A proximal end 107 of the tube 103 is connected to a housing 109 in which are located a plurality of LEDs 13A, 15A and 17A for generating bursts of optical energy.

Each LED produces optical energy having a different preselected wavelength. The numerical values of these wavelengths are not critical so long as these values are precisely known. The hemoglobin isobestic wavelength of 805 nanometers (the "isobestic" wavelength is that wavelength at which $\beta_s = \beta_r$) need not be used. Good results have been obtained by using infrared ("IR"), red and orange LEDs having wavelengths of about 880, 660 and 605 nanometers, respectively.

The LEDs are pulsed at a low duty cycle and high current to maximize the signal-to-noise ratio.

It will be apparent that some other light source, such as filtered incandescent lamps, could be used rather than LEDs to provide light at the desired wavelengths so long as the intensity of the light provided by such a source is stable at least over the length of time required for one calibration and measurement sequence.

A plurality of optical fibers 19A, 21A and 23A serve as guide means for guiding the energy from the LEDs 13A, 15A and 17A, respectively, through the catheter to a proximal side of the receptacle 11A and thence into any blood in the receptacle 11A. The fibers are terminated in a tight bundle within the blood sample and are cleared or polished to provide a good optical interface with the blood.

A receiving means 25A, which includes an optical fiber 111, a mixing ball 113, and another optical fiber 115, receives the optical energy after it has passed through the blood in the receptacle 11A. As best shown in FIG. 3, the fiber 111 receives the energy at a distal side of the receptacle 11A and carries the energy from the receptacle 11A to the mixing ball 113. The fiber 115 carries the energy from the mixing ball 113 back through the catheter to a measurement photocell 27A in the housing 109. The mixing ball 113 is used because the fiber 111 cannot be bent into a U-shape so as to reverse directions within the narrow confines of the tube 103.

The width of the notch 11A between its proximal and distal sides is optimally about 0.025 inches, although a notch having a width between about 0.019 inches and 0.035 inches could be used. The diameters of the various optical fibers should be sufficiently small in relation to the width of the notch 11A as to permit light entering the notch from any of the fibers to spread enough to reach the fiber 111 across the notch. The mixing ball 113 is optimally about 3 times the diameter of the fibers 111 and 115.

The photocell 27A receives the energy from the fiber 115 and provides a signal indicative of the intensity of the energy. The housing 109 includes a plurality of electrical contacts 117 for connection to the computing means 29 of FIG. 1 or the like.

A plurality of optical fibers 31A, 33A and 35A and a reference photocell 37A serve as means to provide a reference indicative of the intensity of the optical energy as provided by the LEDs 13A, 15A and 17A, respectively. The fibers 31A, 33A and 35A are contained entirely within the housing 109 and serve to guide light from their associated LEDs to the photocell 37A.

A plurality of resistors 39A, 41A and 43A serve as a characterization device to provide a characteristic value of the catheter 101 to the computing means 29. As discussed with reference to the embodiment of FIG. 1, this characteristic value might comprise the wavelengths $\lambda_1$, $\lambda_2$ and $\lambda_3$ associated with the LEDs 13A, 15A and 17A and the width d of the receptacle 11A. It will be apparent that a greater or lesser number of resistors than three might be used for this purpose.

Means for flushing the receptacle 11A are preferably provided. This means comprises, for example, a tubelet 119 defining a lumen 121 which extends through the catheter tube 103 from a fixture 123 adjacent the housing 109 to the receptacle 11A. A flushing fluid such as a saline solution can be injected through the lumen 121 into the receptacle 11A to flush the receptacle and remove any clotted blood or the like.

Figures 5, 6:
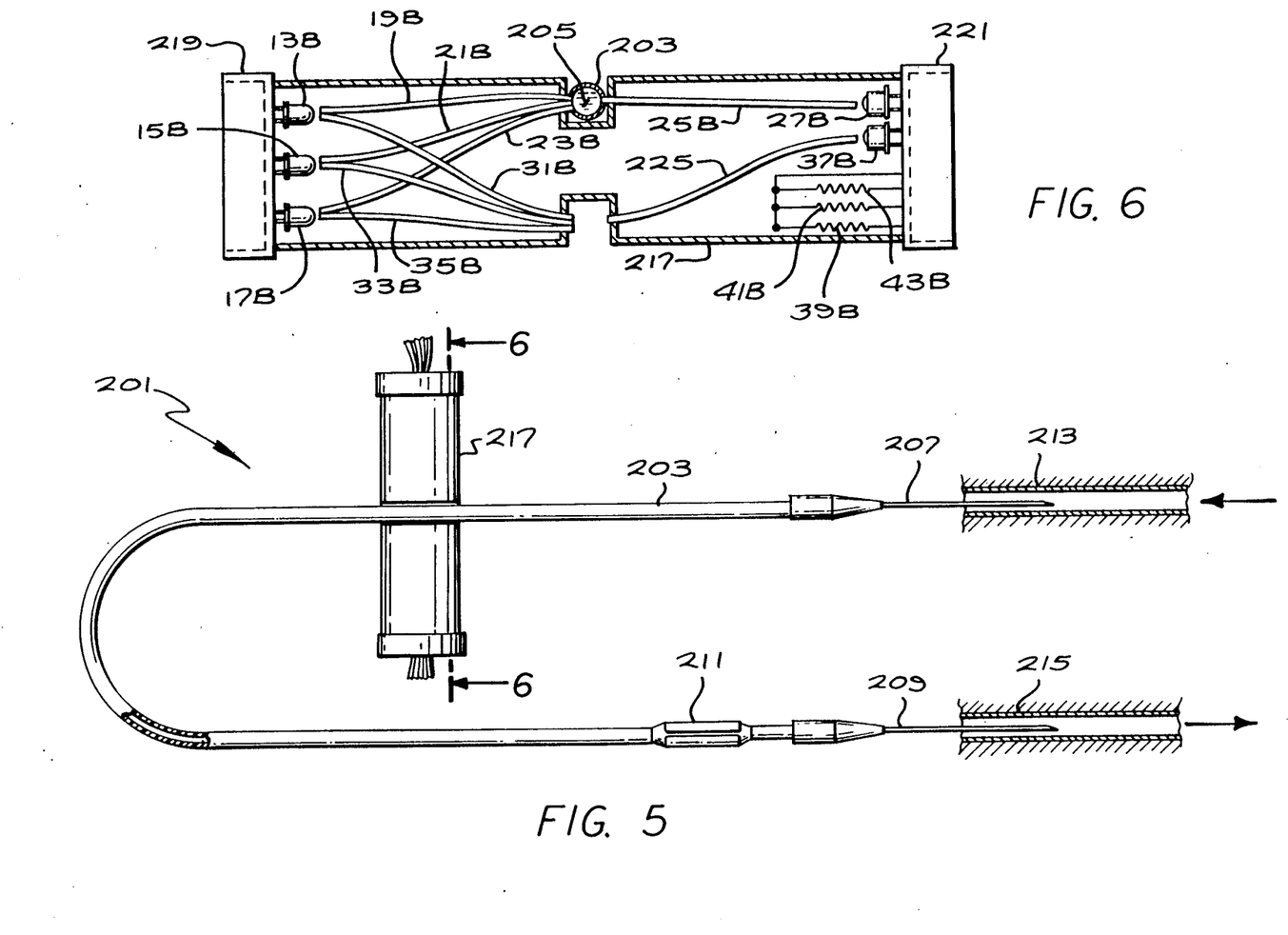
FIG. 5 is a pictorial diagram of an alternate embodiment of the apparatus of FIG. 1 as adapted for measuring a parameter of blood which is circulating outside the body of a patient.
FIG. 6 is a sectional view taken along the line 6—6 of FIG. 5.

An alternate embodiment of the invention generally designated 201 is shown in FIGS. 5 and 6. Several of the components of this embodiment are analogous to components shown in the more general embodiment of FIG. 1, and for convenience such components are identified by the same reference numerals as their FIG. 1 counterparts plus the suffix "B".

The apparatus 201 includes means such as a portion of a clear-walled tube 203 defining a measurement chamber 205; circulation means such as the tube 203 for circulating blood through the chamber 205; optical energy generating means such as LEDs 13B, 15B and 17B; guide means such as optical fibers 19B, 21B and 23B for guiding the energy through any blood in the chamber 205; receiving means such as an optical fiber 25B for receiving the energy after it has passed through the blood in the chamber 205; and measuring means such as a photocell 27B for measuring the intensity of each burst of received energy. Computing means 29 or the like is used to compute the oxygen saturation s and hematocrit h of the blood.

A pair of hypodermic needles 207 and 209 are preferably used for withdrawing blood from, and returning blood to, the patient.

Optional constriction means such as a constrictor 211 creates a pressure drop as the blood circulates through the tube 203. This permits the blood to be withdrawn from an artery 213 at a relatively high pressure and returned to a vein 215 at a relatively low pressure.

The LEDs 13B, 15B and 17B and the photocell 27B are contained within a housing 217. Electrical contacts (not shown) in opposing ends 219 and 221 of the housing 217 are provided for connection of the various components in the housing to the computing means.

A plurality of optical fibers 31B, 33B and 35B and a photocell 37B serve as means to provide a reference indicative of the intensity of the optical energy as provided by the LEDs 13B, 15B and 17B, respectively. The fibers 31B, 33B and 35B preferably extend from their respective LEDs to a first side of a gap 223 defined in the housing 217 and having a width similar to the width of the chamber 205. Another fiber 225 carries light from an opposing side of the gap 223 to the photocell 37B.

A plurality of resistors 39B, 41B and 43B serve as a characterization device to provide information such as wavelengths and the width of the chamber 205.

The characterization resistors are selected during manufacture to indicate the wavelengths of the LEDs and the width of the notch or chamber, thereby making it unnecessary to precisely control these quantities. This helps make it possible to manufacture the catheter 101 or the apparatus 201 economically so as to facilitate one-time use and disposal. It will be apparent that if desired the wavelengths of the LEDs and the width of the notch or chamber may be precisely controlled during manufacture, the values of the wavelengths and width stored in the memory 49, and the characterization device omitted.

E. THE METHOD OF THE INVENTION

1. In General

Figure 7:
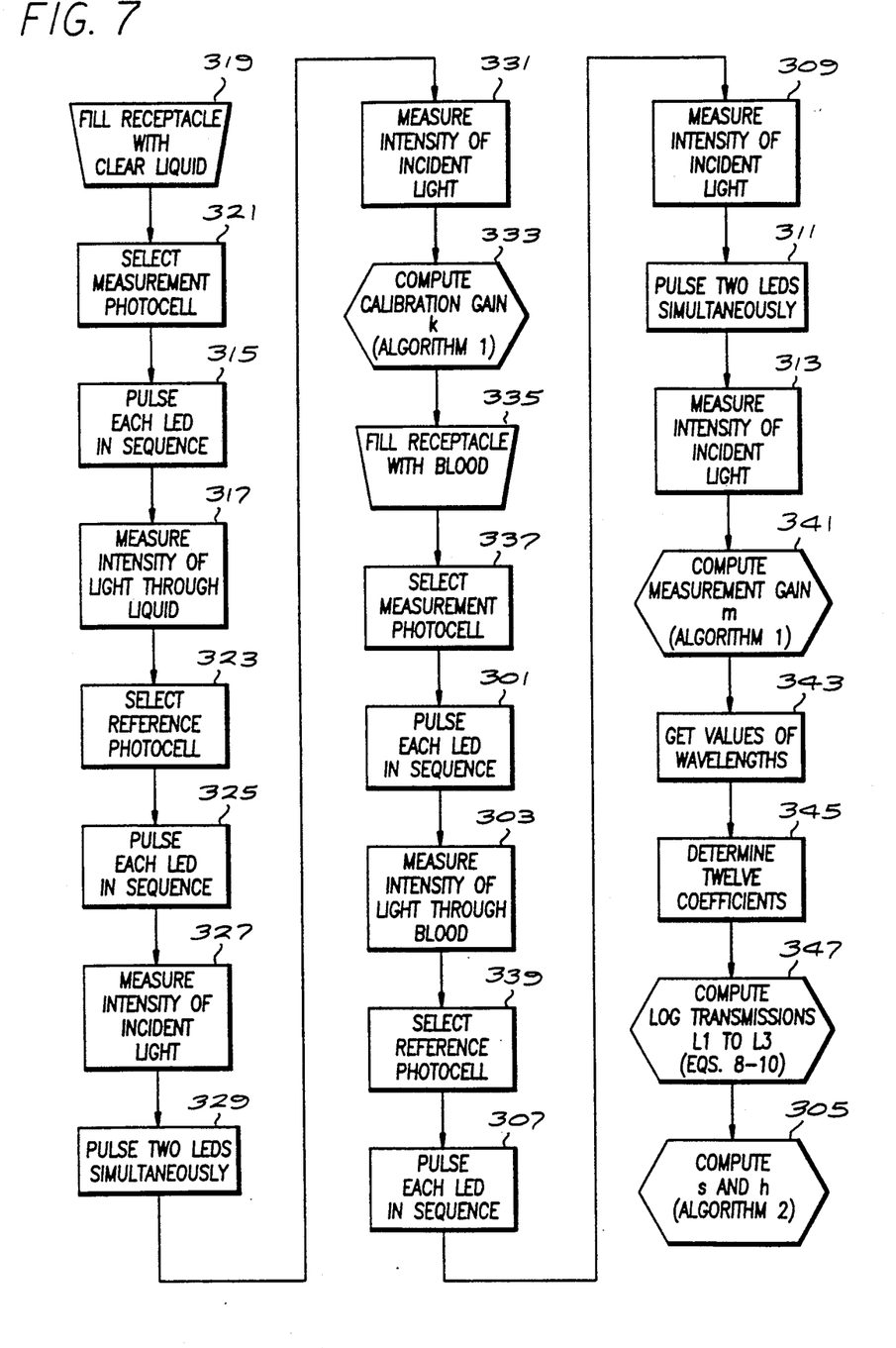
FIG. 7 is a flowchart depicting the steps of measuring a blood parameter according to the invention.

As depicted in flowchart form in FIG. 7, a method according to the invention of measuring a parameter of a sample of blood includes the steps of passing sequential bursts of optical energy through a sample of blood from a patient, each burst characterized by one of a plurality of preselected wavelengths (block 301); measuring the intensity of each burst of energy after it has passed through the sample (block 303); and computing a parameter of the sample of blood according to the measured intensities of the received bursts of energy and a plurality of predetermined molecular extinction coefficients and optical scattering coefficients (block 305).

In one embodiment the bursts of energy are passed through blood at a preselected location within the body of the patient. In another embodiment the bursts of energy are passed through blood as the blood circulates through a circulation path which extends in a loop out of and back into the body of the patient.

Preferably, the method includes the steps of providing a reference indicative of the intensity of the optical energy as provided by the generating means and utilizing said reference in computing the parameter of the blood (blocks 307, 309, 311 and 313). Additionally, the steps of passing sequential bursts of energy through a calibration fluid, each burst characterized by one of said wavelengths (block 315); measuring the intensity of each burst of energy after it has passed through the calibration fluid (block 317); and utilizing these measured calibration intensities in computing the parameter of the blood are also performed.

2. Calibration

The apparatus should be calibrated immediately prior to use. This is accomplished, for example, by filling the receptacle 11 with a clear liquid such as saline solution (block 319). The amplifier 45 is connected to the measurement photocell 27 (block 321). The three LEDs are pulsed in sequence (block 315) and the intensity of the amplifier output is measured while each LED is illuminated (block 317). Then the amplifier is connected to the reference photocell 37 (block 323), the LEDs are pulsed again (block 325), and the intensity of the amplifier output corresponding with the illumination of each LED is again measured (block 327). Finally, two of the LEDs are pulsed simultaneously (block 329) and the intensity of the amplifier output is measured (block 331). The results of these measurements may be expressed in tabular form as follows:

TABLE 1

| WAVE-LENGTH | COLOR | PATH of LIGHT | INTENSITY |
|---|---|---|---|
| $\lambda_1$ | IR | Receptacle (clear liquid) | p |
| $\lambda_2$ | Red | Receptacle (clear liquid) | q |
| $\lambda_3$ | Orange | Receptacle (clear liquid) | r |
| $\lambda_1$ | IR | Reference | t |
| $\lambda_2$ | Red | Reference | u |
| $\lambda_3$ | Orange | Reference | v |
| $\lambda_1 + \lambda_2$ | IR + Red | Reference | w | where:
- p = measured intensity of light at $\lambda_1$ through clear liquid;
- q = measured intensity of light at $\lambda_2$ through clear liquid;
- r = measured intensity of light at $\lambda_3$ through clear liquid;
- t = measured intensity of light at $\lambda_1$ through reference path;
- u = measured intensity of light at $\lambda_2$ through reference path;
- v = measured intensity of light at $\lambda_3$ through reference path; and
- w = measured intensity of light at $\lambda_1$ and $\lambda_2$ through reference path.

Figure 8:
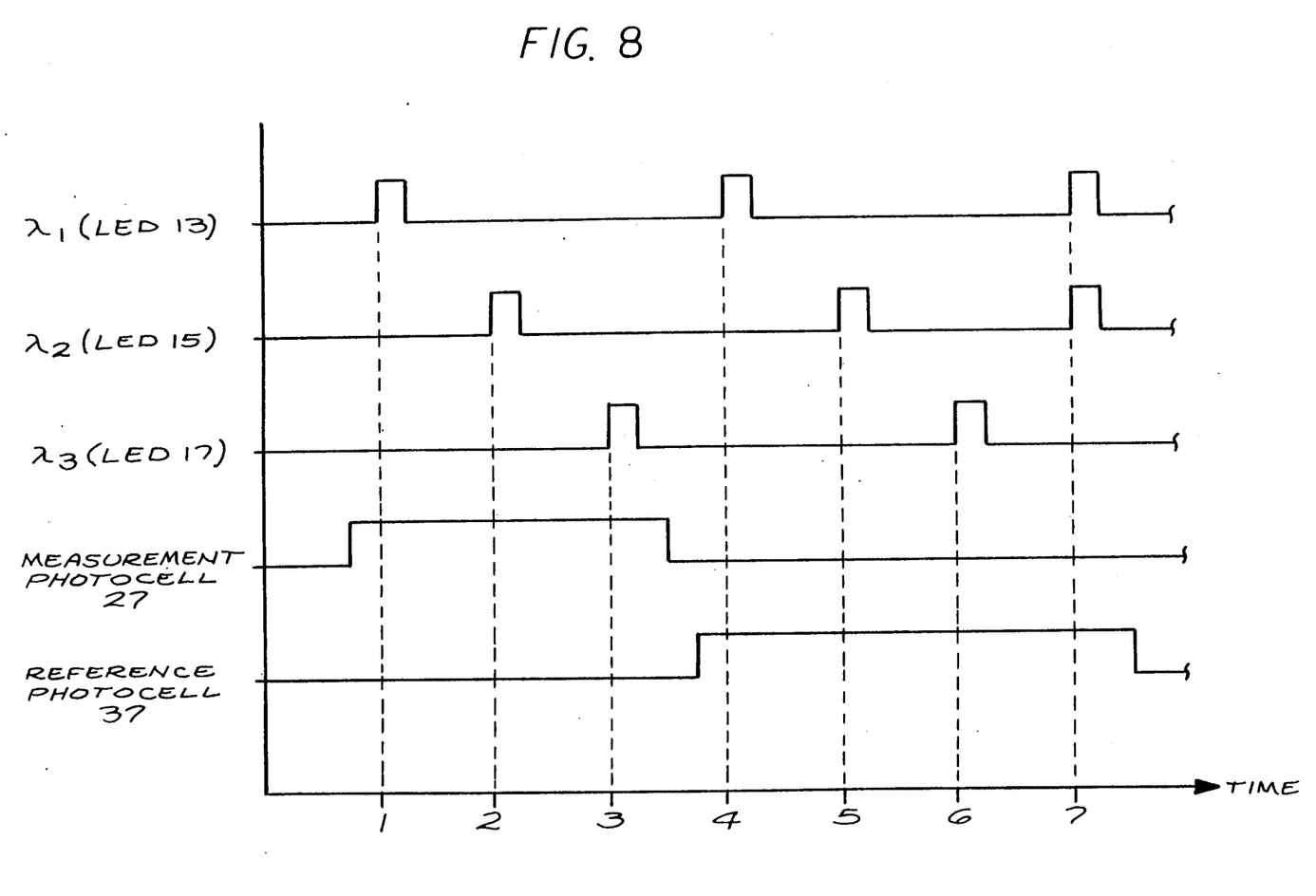
FIG. 8 is a timing diagram showing the time sequence of activation of the LEDs of FIG. 1.

The above sequence of operation is depicted in timing chart form in FIG. 8. At the beginning of a measurement, just prior to a time $T_1$ the measurement photocell 27 is activated (connected to the amplifier 45); it remains activated until after a later time $T_3$. At time $T_1$ LED 13 (wavelength $\lambda_1$) is pulsed, at time $T_2$ LED 15 (wavelength $\lambda_2$) is pulsed and at time $T_3$ LED 17 (wavelength $\lambda_3$) is pulsed. Then the measurement photocell 27 is deactivated and the reference photocell 37 is activated. Then at time $T_4$ LED 13 (wavelength $\lambda_1$) is pulsed, at time $T_5$ LED 15 (wavelength $\lambda_2$) is pulsed and at time $T_6$ LED 17 (wavelength $\lambda_3$) is pulsed. Then at time $T_7$ LEDs 13 and 15 are pulsed simultaneously.

Next, a system calibration gain k is calculated by solving the following Equation (6) for k:

$$\sqrt[k]{10^t} + \sqrt[k]{10^u} = \sqrt[k]{10^w} \tag{6}$$

where:
- $k$ = system calibration gain,
- $t$ = reference path output from first (e.g., infra-red) LED,
- $u$ = reference path output from second (red) LED, and
- LED, = reference path output from first and second LEDs.

Equation (6) can be solved by iteration according to the following Algorithm 1 (block 333):

| ALGORITHM 1 |
|---|
| 10    IF u > t THEN exchange u and t in statements 20 and 25 |
| 15    LET k = 1 |

-continued

ALGORITHM 1

```
20    LET j = $\sqrt[k]{10^u}$

25    LET n = $\sqrt[k]{10^w} - \sqrt[k]{10^t}$

30    LET k = k$\sqrt[4]{n/j}$

35    GOTO statement 20
``` where j and n are dummy variables. The algorithm is allowed to loop as many times as necessary until k remains constant to within a desired degree of accuracy (32 iterations should be sufficient).

3. Measurement

Next the receptacle is filled with a sample of the blood to be analyzed (block 335). If the catheter embodiment 101 is being used, it is inserted into the body and the notch 11A is guided to the desired location (e.g., a ventricle of the heart). The notch 11A is preferably flushed with saline solution after reaching the desired position to remove any clotted blood or the like, or any blood carried along from some other part of the body, and then is allowed to fill with blood at the desired location.

If the apparatus 201 is being used, a flow of blood through the chamber 205 is established, for example by inserting the needles 207 and 209 into the patient's artery 213 and vein 215, respectively.

Next the amplifier is connected to the measurement photocell (block 337). The three LEDs are pulsed in sequence (block 301) and the intensity of the amplifier output is measured while each LED is illuminated (block 303). Then the amplifier is connected to the reference photocell (block 339), the LEDs are pulsed again (block 307), and the intensity of the amplifier output corresponding with the illumination of each LED is again measured (block 309). Finally, two of the LEDs are pulsed simultaneously (block 311) and the intensity of the amplifier output is measured (block 313). This sequence of operation of the LEDs is similar to the sequence depicted in FIG. 8 as utilized during the calibration sequence discussed above. The results of these measurements may be expressed in tabular form as follows:

TABLE 2

| WAVELENGTH | COLOR | PATH of LIGHT | INTENSITY |
|---|---|---|---|
| $\lambda_1$ | IR | Gap (blood) | P |
| $\lambda_2$ | Red | Gap (blood) | Q |
| $\lambda_3$ | Orange | Gap (blood) | R |
| $\lambda_1$ | IR | Reference | T |
| $\lambda_2$ | Red | Reference | U |
| $\lambda_3$ | Orange | Reference | V |
| $\lambda_1 + \lambda_2$ | IR + Red | Reference | W | where:
P = measured intensity of light at $\lambda_1$ through blood;
Q = measured intensity of light at $\lambda_2$ through blood;
R = measured intensity of light at $\lambda_3$ through blood;
T = measured intensity of light at $\lambda_1$ through reference path;
U = measured intensity of light at $\lambda_2$ through reference path;
V = measured intensity of light at $\lambda_3$ through reference path; and
W = measured intensity of light at $\lambda_1$ and $\lambda_2$ through reference path.

A system measurement gain $m$ is calculated by solving the following Equation (7) for $m$:

$$\sqrt[m]{10^T} + \sqrt[m]{10^U} = \sqrt[m]{10^W} \tag{7}$$

where:
$m$ = system measurement gain,
$T$ = reference path output from first (e.g., infra-red) LED,
$U$ = reference path output from second (red) LED, and
$W$ = reference path output from first and second LEDs.

Equation (7) can be solved by means of Algorithm 1 as set forth above (block 341). The system measurement gain m is recalculated at each measurement to compensate for any drift in the amplifier 45 or in any of the other components.

Information giving the wavelength of each LED is read from the characterization devices (block 343) and is used to determine, by extrapolation from the stored table of molecular extinction coefficients (block 345), numerical values for each of the following twelve coefficients:

| | |
|---|---|
| $\beta_{r1}$ | molecular extinction coefficient for reduced hemoglobin at $\lambda_1$ (e.g., infra-red); |
| $\beta_{s1}$ | molecular extinction coefficient for oxyhemoglobin at $\lambda_1$; |
| $\beta_{r2}$ | molecular extinction coefficient for reduced hemoglobin at $\lambda_2$ (e.g., red); |
| $\beta_{s2}$ | molecular extinction coefficient for oxyhemoglobin at $\lambda_2$; |
| $\beta_{r3}$ | molecular extinction coefficient for reduced hemoglobin at $\lambda_3$ (e.g., orange); |
| $\beta_{s3}$ | molecular extinction coefficient for oxyhemoglobin at $\lambda_3$; |
| $\beta_{z1(s=1)}$ | optical scattering coefficient at $\lambda_1$ for s = 1; |
| $\beta_{z2(s=1)}$ | optical scattering coefficient at $\lambda_2$ for s = 1; |
| $\beta_{z3(s=1)}$ | optical scattering coefficient at $\lambda_3$ for s = 1; |
| $\beta_{z1(s=0)}$ | optical scattering coefficient at $\lambda_1$ for s = 0; |
| $\beta_{z2(s=0)}$ | optical scattering coefficient at $\lambda_2$ for s = 0; |
| $\beta_{z3(s=0)}$ | optical scattering coefficient at $\lambda_3$ for s = 0; |

Next, log transmissions $L_1$, $L_2$ and $L_3$, corresponding with $\lambda_1$, $\lambda_2$ and $\lambda_3$ respectively, are computed (block 347) as follows:

$$L_1 = P - T - \frac{m}{k}(p - t) \tag{8}$$

$$L_2 = Q - U - \frac{m}{k}(q - u) \tag{9}$$

$$L_3 = R - V - \frac{m}{k}(r - v) \tag{10}$$

It will be recalled that Equations (5a), (5b) and (5c) constitute a set of three equations in which s and h are unknown and in which optical scattering coefficients $\beta_{z1(s)}$, $\beta_{z2(s)}$ and $\beta_{z3(s)}$ are functions of s and therefore are also unknown because s has not yet been determined. The following Algorithm 2 can be used to find s and h by successive approximations, utilizing the predetermined values of the optical scattering coefficients for s=0 and s=1 and an assumed initial value for s (block 305):

ALGORITHM 2

SET INITIAL CONDITIONS:
```
10    LET $\beta_1$ = m$\beta_{r1}$;
15    LET $\beta_2$ = m$\beta_{s1}$;
20    LET $\beta_3$ = m$\beta_{r2}$;
25    LET $\beta_4$ = m$\beta_{s2}$;
30    LET $\beta_5$ = m$\beta_{r3}$;
35    LET $\beta_6$ = m$\beta_{s3}$;
40    LET $\beta_7$ = m$\beta_{z1(s=1)}$;
45    LET $\beta_8$ = m$\beta_{z2(s=1)}$;
```

-continued

ALGORITHM 2

| 50 | LET $\beta_9 = m\beta_{z3(s=1)}$; |
| --- | --- |
| 55 | LET $\beta_{10} = m\beta_{z1(s=0)}$; |
| 60 | LET $\beta_{11} = m\beta_{z2(s=0)}$; |
| 65 | LET $\beta_{12} = m\beta_{z3(s=0)}$; |
| 70 | LET s = 0.75; |
| 75 | LET x = 40d; |
|  | PERFORM CALCULATIONS: |
| 80 | LET $\beta_{13} = \beta_{10} - s(\beta_{10} - \beta_7)$ |
| 85 | LET $\beta_{14} = \beta_{11} - s(\beta_{11} - \beta_8)$ |
| 90 | LET $\beta_{15} = \beta_{12} - s(\beta_{12} - \beta_9)$ |
| 95 | LET $y = \dfrac{-L_1 - x[s(\beta_2 - \beta_1) + \beta_1]}{\beta_{13}}$ |
| 100 | LET $s = \dfrac{[L_1 - L_2 + y(\beta_{13} - \beta_{14})](\beta_3 - \beta_5) + [L_2 - L_3 + y(\beta_{14} - \beta_{15})](\beta_3 - \beta_1)}{[L_1 - L_2 + y(\beta_{13} - \beta_{14})](\beta_6 - \beta_5 - \beta_4 + \beta_3) + [L_2 - L_3 + y(\beta_{14} - \beta_{15})](\beta_4 - \beta_3 - \beta_2 + \beta_1)}$ |
| 105 | LET $x = \dfrac{L_1 - L_2 + y(\beta_{13} - \beta_{14})}{\beta_3 - \beta_1 + s(\beta_4 - \beta_3 - \beta_2 + \beta_1)}$ |
| 110 | GOTO Statement 80 |
| 115 | LET $h = \dfrac{x}{d}$ | where x and y are dummy variables. Algorithm 2 is allowed to loop as many times as necessary to achieve the desired degree of accuracy. 16 iterations will usually be sufficient.

From the foregoing it will be appreciated that the invention provides a method and apparatus for accurately measuring parameters such as oxygen level and hematocrit of the blood of a patient in real time and at any desired location in the body of the patient or in blood circulating outside the patient. The apparatus of the invention is particularly well adapted for use during critical surgical procedures. The accuracy of the invention is enhanced by provision for reference and calibration measurements and by the use of optical scattering coefficients of the blood. Performance is not adversely affected by any reflections from blood vessel walls or the like. Any chance of infection by use of the invention is minimized because the apparatus is economical to manufacture and hence is disposable after a single use.

Although several specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

I claim:

1. Apparatus for measuring a parameter of a sample of blood, the apparatus comprising:
   means defining a receptacle for insertion into a body to a desired location and for receiving the sample of blood at said location;
   generating means for generating bursts of optical energy, each burst characterized by one of a plurality of preselected wavelengths;
   guide means for guiding the energy into the sample of blood in the receptacle;
   receiving means for receiving the energy after it has passed through the blood in the receptacle;
   measuring means for measuring the intensity of each burst of received energy;
   a memory having a molecular extinction coefficient and an optical scattering coefficient stored therein; and
   computing means, operative to read the memory to obtain the molecular extinction coefficient and the optical scattering coefficient and to compute the desired parameter of the blood according to the measured intensities of the received bursts of energy and according to said coefficients.

2. Apparatus according to claim 1 wherein the measuring means includes means to provide a reference indicative of the intensity of the optical energy as provided by the generating means and wherein the computing means computes the parameter according to said reference.

3. Apparatus according to claim 1 wherein the parameter to be measured comprises oxygen saturation level.

4. Apparatus according to claim 1 wherein the parameter to be measured comprises hematocrit.

5. Apparatus according to claim 1 and further comprising a characterization device adapted to provide a characteristic value of the apparatus to the computing means whereby the parameter is computed according to said characteristic value.

6. Apparatus according to claim 5 wherein the characteristic value comprises the width of the receptacle between the guide means and the receiving means.

7. Apparatus according to claim 5 wherein the characteristic value comprises the values of the preselected wavelengths.

8. The apparatus of claim 1 wherein the receiving means is also for directly receiving the energy on the opposite side of the receptacle from the guide means after said energy has passed through the blood in the receptacle.

9. The apparatus of claim 8 wherein:
   the guide means comprises a first optical fiber which emits said optical energy into the receptacle; and
   the receiving means comprises a second optical fiber disposed on the opposite side of the receptacle from the first optical fiber for receiving the emitted energy.

10. The apparatus of claim 9 wherein:
   the receiving means further comprises a third optical fiber and a mixing ball connected between the second and third optical fibers which conducts the received energy from the second optical fiber to the third optical fiber; and
   the computing means is also for computing the parameter from the optical energy conducted by the third optical fiber.

11. The apparatus of claim 8 wherein the plurality of preselected wavelengths comprise three wavelengths.

12. The apparatus of claim 1 wherein:
   the computing means is also for deriving molecular extinction coefficients and optical scattering coefficients from said stored molecular extinction coefficient and optical scattering coefficient and from said preselected wavelengths and for computing said parameter according to said derived coefficients.

13. A catheter for measuring the oxygen saturation and hematocrit of a sample of blood at a desired location in a body of a patient, the catheter comprising:
   an elongated catheter tube adapted for insertion into a body of a patient, a distal extremity of the tube guidable to a desired location in the body and having a receptacle for receiving a sample of blood at said location;
   generating means for generating bursts of optical energy, each burst characterized by one of a plurality of preselected wavelengths;
   guide means for guiding the energy into any blood in the receptacle;
   receiving means for receiving the energy after it has passed through the blood in the receptacle;
   measuring means for measuring the intensity of each burst of received energy;
   a memory having a molecular extinction coefficient and an optical scattering coefficient stored therein; and
   computing means, operative to read the memory to obtain the molecular extinction coefficient and the optical scattering coefficient and to compute the oxygen saturation and hematocrit of the blood at said location according to the measured intensities of the received bursts of energy and said coefficients.

14. A catheter according to claim 13 and further comprising means for flushing the receptacle.

15. A catheter according to claim 14 wherein the flushing means comprises a tubelet defining a lumen extending through the catheter to the receptacle whereby a flushing fluid can be injected through the lumen into the receptacle to flush the receptacle.

16. A catheter according to claim 13 wherein the measuring means includes means to provide a reference indicative of the intensity of the optical energy as provided by the generating means and wherein said reference is utilized by the computing means in performing its computations.

17. A catheter according to claim 13 and further comprising a characterization device adapted to provide a characteristic value of the catheter to the computing means for use in performing its computations.

18. A catheter according to claim 17 wherein the characteristic value comprises the width of the receptacle between the guide means and the receiving means.

19. A catheter according to claim 13 wherein the generating means comprises a plurality of light-emitting diodes each operative to generate a burst of optical energy at a different one of the preselected wavelengths.

20. A catheter according to claim 19 and further comprising a characterization device adapted to provide the values of the wavelengths of the optical energy to the computing means for use in performing its computations.

21. A catheter according to claim 13 wherein the guide means comprises a first optical fiber which emits said optical energy into the receptacle.

22. The catheter of claim 21 wherein the receiving means is also for directly receiving the energy on the opposite side of the receptacle from the guide means after it has passed through the blood in the receptacle.

23. The catheter of claim 22 wherein:
   the receivig means comprises:
      a second optical fiber disposed on the opposite side of the receptacle from the first optical fiber for receiving the emitted energy;
      a third optical fiber; and
      a mixing ball connected between the second and third optical fibers for conducting the received energy from the second optical fiber to the third optical fiber; and
   the computing means is also for computing the oxygen saturation and the hematocrit from the optical energy conducted by the third optical fiber.

24. A catheter according to claim 13 wherein the receiving means comprises a mixing ball, a first optical fiber extending distally from the receptacle and terminating in the mixing ball, and a second optical fiber extending from the mixing ball to the measuring means.

25. The catheter of claim 13 wherein:
   the computing means is also for deriving molecular extinction coefficients and optical scattering coefficients from said stored molecular extinction coefficient and optical scattering coefficient and from said preselected wavelengths and for computing said parameter according to said derived coefficients.

26. A catheter for measuring the oxygen saturation and hematocrit of a sample of blood at a desired location in a body of a patient, the cathereter comprising:
   an elongated catheter tube adapted for insertion into the body of the patient, a distal extremity of the tube guidable to the desired location in the body and having a receptacle for receiving a sample of blood at said location;
   a light source adapted to provide sequential bursts of optical energy of a plurality of preselected wavelengths;
   a first optical fiber coupled to the light source to couple the bursts of optical energy to the sample of blood in the receptacle;
   a second optical fiber disposed at the opposite side of the receptacle from the first fiber and which directly receives the bursts of optical energy from the first fiber after they have passed through the sample of blood in the receptacle;
   a third optical fiber coupled to the second optical fiber for conducting the energy received by the second optical fiber;
   a characterization device which stores a value representing the distance between the first and second optical fibers and values representing the preselected wavelengths;
   a memory having a plurality of molecular extinction coefficients and optical scattering coefficients stored therein; and
   a processor adapted to read the values from the characterization device and read the plurality of molecular extinction coefficients and optical scattering coefficients stored in the memory and adapted to derive a molecular coefficient of extinction and an optical scattering coefficient for each of the preselected wavelengths, and also adapted to receive the optical energy conducted by the third optical fiber and to compute the oxygen saturation and hematocrit of the sample of blood according to the intensities of the received bursts of energy, the characterization values and the derived coefficients.

27. A method of measuring a parameter of a sample of blood, the method comprising:

disposing a receptacle at a selected location in the body of a patient;

collecting the sample of blood in the receptacle;

passing sequential bursts of optical energy through the sample of blood, each burst characterized by one of a plurality of preselected wavelengths;

storing a predetermined molecular extinction coefficient and an optical scattering coefficient;

measuring the intensity of each burst of energy after it has passed through the sample;

reading the stored coefficients; and computing a parameter of the sample blood according to the measured intensities of the received bursts of energy and according to said predetermined molecular extinction coefficient and optical scattering coefficient.

28. A method according to claim 27 and further comprising the step of providing a reference indicative of the intensity of the optical energy as provided to the sample and wherein said step of computing further comprises utilizing said reference in computing the parameter of the blood.

29. A method according to claim 27 wherein the bursts of energy are passed through blood as the blood circulates through a circulation path which extends in a loop out of the body of the patient and back into the body.

30. A method according to claim 27 and further comprising:

passing sequential bursts of energy through a calibration fluid, each burst characterized by one of said wavelengths;

measuring the intensity of each burst of energy after it has passed through the calibration fluid; and utilizing these measured calibration intensities in computing the parameter of the blood.

31. A method according to claim 27 wherein the parameter to be measured comprises oxygen saturation level.

32. A method according to claim 27 wherein the parameter to be measured comprises hematocrit.

33. The method of claim 27 wherein:

the step of measuring the intensity comprises directly receiving the optical energy on the opposite side of the receptacle from the position at which the bursts were emitted.

34. The method of claim 33 wherein:

the step of passing sequential bursts comprises emitting the optical energy into the receptacle with a first optical fiber; and the step of measuring comprises:

receiving the optical energy with a second optical fiber after it has passed through the sample of blood; and conducting the optical energy received by the second optical fiber to a third optical fiber through a mixing ball disposed between the second and third optical fibers.

35. The method of claim 34 wherein the step of passing sequential bursts comprises passing sequential bursts of optical energy of three preselected wavelengths.

36. The method of claim 27 wherein the step of computing comprises:

deriving molecular extinction coefficients and optical scattering coefficients from said stored molecular extinction coefficient and said optical scattering coefficient and from said preselected wavelengths; and computing said parameter according to said derived coefficients.

37. The method of claim 36 wherein the step of storing the coefficients comprises:

measuring a transmittance spectrum for whole blood which is one-hundred percent saturated with oxygen;

measuring a transmittance spectrum for whole blood which is much less than one-hundred percent saturated with oxygen;

measuring a transmittance spectrum for hemolyzed blood which is one-hundred percent saturated with oxygen;

measuring a transmittance spectrum for hemolyzed blood which is much less than one-hundred percent saturated with oxygen;

determining a molecular extinction coefficient and an optical scattering coefficient from comparisons of said spectra; and storing said coefficients.

38. The method of claim 37 wherein:

the steps of measuring comprise measuring said spectra at a plurality of wavelengths;

determining a molecular extinction coefficient and an optical scattering coefficient for each wavelength; and storing each determined coefficient.

39. The method of claim 38 wherein the step of computing comprises:

reading said stored plurality of coefficients;

deriving molecular extinction coefficients and optical scattering coefficients for each of the preselected wavelengths according to the read plurality of coefficients.

40. The method of claim 39 wherein the parameter to be measured comprises oxygen saturation level and hematocrit and wherein:

the step of computing comprises:

successively approximating the oxygen saturation level and hematocrit;

comparing each approximation with the previous approximation; and providing a value for oxygen saturation level and hematocrit when the present approximation differs from the previous aproximation by less than a predetermined amount.

* * * * *